(12) United States Patent
Astier et al.

(10) Patent No.: US 9,543,118 B2
(45) Date of Patent: Jan. 10, 2017

(54) GOLD ION BEAM DRILLED NANOPORES MODIFIED WITH THIOLATED DNA ORIGAMIS

(71) Applicant: International Business Machines Corporation, Armonk, NY (US)

(72) Inventors: Yann Astier, Irvington, NY (US); Joshua T. Smith, Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/744,141

(22) Filed: Jun. 19, 2015

(65) Prior Publication Data

US 2016/0322197 A1    Nov. 3, 2016

Related U.S. Application Data

(63) Continuation of application No. 14/700,331, filed on Apr. 30, 2015.

(51) Int. Cl.
*G01N 27/00* (2006.01)
*H01J 37/305* (2006.01)
*B23K 15/08* (2006.01)
*C23C 14/48* (2006.01)
*C23C 14/58* (2006.01)

(52) U.S. Cl.
CPC ........... *H01J 37/3056* (2013.01); *B23K 15/08* (2013.01); *C23C 14/48* (2013.01); *C23C 14/5846* (2013.01)

(58) Field of Classification Search
CPC . G01N 33/54386; H01J 37/31; H01J 37/3056; C23C 14/48; C23C 14/5846; B23K 15/08
USPC ...................................................... 422/82.03
See application file for complete search history.

(56) References Cited

PUBLICATIONS

Stoloff et al. (Curr Opin Biotechnol. Aug. 2013; 24(4): 699-704).*
Pathak vol. 100 (Appl Phys Lett. Jan. 2012).*
Gierak et al. (Microelectronic Engineering vol. 87, Dec. 2009; 1386-1390).*
Thacker, V. V. (2013). "DNA origami based assembly of gold nanoparticle dimers for surface-enhanced Raman scattering." Nature Communications. 5:3448. 1-7.*
Stoloff, D. (2013). "Recent trends in nanopores for biotechnology." Curr Opin Biotechnol. 24(4): 699-704.*

(Continued)

*Primary Examiner* — Dennis M White
(74) *Attorney, Agent, or Firm* — Cantor Colburn LLP; Vazken Alexanian (57) ABSTRACT

A nanopore structure includes an aperture extending from a first surface to a second surface of a substrate, the aperture having a wall comprising gold ions embedded in the substrate, the wall defining a first diameter; a first deoxyribonucleic acid (DNA) layer including a thiolated DNA strand covalently bonded to the embedded gold ions within the wall of the aperture; and a second DNA layer hydrogen bonded to the first DNA layer, the second DNA layer defines a substantially cylindrical nanopore that defines a second diameter within the wall of the aperture, the second DNA layer including a single-stranded DNA strand; wherein the second diameter is less than the first diameter.

10 Claims, 7 Drawing Sheets

(56) References Cited

PUBLICATIONS

Pathak, B. (2012). "Double-functionalized nanopore-embedded gold electrodes for rapid DNA sequencing." Applied Physics Letters 100, 023701.*

Li et al, "Fabrication and verification of DNA functionalized nanopore with gold layer embedded structure for bio-molecular sensing" 2011 IEEE Nanotechnology Materials and Devices Conference, Oct. 18-21, 2011, Jeju, Korea. pp. 168-171.*

Astier, Yann, et al.; "Gold Ion Beam Drilled Nanopores Modified With Thiolated Origamis"; U.S. Appl. No. 14/700,331, filed Apr. 30, 2015.

List of IBM Patents or Patent Applications Treated As Related—Date Filed: Jun. 6, 2016; 1 page.

* cited by examiner

GOLD ION BEAM DRILLED NANOPORES MODIFIED WITH THIOLATED DNA ORIGAMIS

PRIORITY

This application is a continuation of and claims priority from U.S. patent application Ser. No. 14/700,331, filed on Apr. 30, 2015, entitled "GOLD ION BEAM DRILLED NANOPORES MODIFIED WITH THIOLATED DNA ORIGAMIS", the entire contents of which are incorporated herein by reference.

BACKGROUND

The present disclosure generally relates to nanopores, and more specifically, to artificial nanopores.

Nanopore development for single molecule sensing applications is a rapidly growing field. Natural nanopores are gene-expressed and generally form an aperture, or channel, between two lipid membranes. Various molecules, for example, proteins, deoxyribonucleic acid (DNA), and other small molecules, traverse membranes through the nanopore. When a potential difference is generated across the lipid bilayer, ionic current can be monitored. A change in ionic current can indicate that a molecule(s) is binding to and/or moving through the nanopore. Different types of molecules can demonstrate different ionic current changes.

Natural or biological nanopores, such as alpha-hemolysin, can detect and identify DNA bases for sequencing applications. These nanopores also can be used for detecting drugs, explosives, or chemical warfare agents at the single molecule level.

Protein nanopores are nanopores that are genetically engineered to recognize different molecules, for example, different DNA bases. These genetically engineered nanopores can provide data with relatively high signals and resolutions. Like natural nanopores, however, genetically engineered nanopores rely on a suspended lipid bilayer for device operation.

Artificial nanopores do not rely on a lipid membrane. Artificial nanopores can include, for example, silicon nitride (SiN) or silicon oxide (SiO) and are generally apertures through two solid surfaces.

SUMMARY

In one embodiment of the present disclosure, a nanopore structure includes an aperture extending from a first surface to a second surface of a substrate, the aperture having a wall including gold ions embedded in the substrate, the wall defining a first diameter; a first deoxyribonucleic acid (DNA) layer comprising a thiolated DNA strand covalently bonded to the embedded gold ions within the wall of the aperture; and a second DNA layer hydrogen bonded to the first DNA layer, the second DNA layer defines a substantially cylindrical nanopore that defines a second diameter within the wall of the aperture, the second DNA layer including a single-stranded DNA strand; wherein the second diameter is less than the first diameter.

In another embodiment, a nanopore structure includes an aperture extending from a first surface to a second surface of a substrate, the aperture having a wall including gold ions embedded in the substrate, the wall defining a first diameter; a first deoxyribonucleic acid (DNA) layer comprising a thiolated DNA strand covalently bonded to the embedded gold ions within the wall of the aperture; a second DNA layer hydrogen bonded to the first DNA layer, the second DNA layer defines a substantially cylindrical nanopore that defines a second diameter within the wall of the aperture, the second DNA layer including a single-stranded DNA strand; and a biomolecule binding site on the single-stranded DNA strand, the biomolecule binding site being a chemical functional group that is chemically bonded to the single-stranded DNA strand or a DNA sequence within the single-stranded DNA strand; wherein the second diameter is less than the first diameter.

Yet, in another embodiment, a method for making a nanopore structure includes drilling with a gold ion beam to define an aperture through a substrate and to introduce and embed gold ions within a wall of the aperture, the wall defining a first diameter; bonding a thiolated DNA strand to the embedded gold ions with a covalent bond; and hydrogen bonding a single-stranded DNA strand to the thiolated DNA strand with a covalent bond to define a substantially cylindrical nanopore, the substantially cylindrical nanopore defining a second diameter within the aperture; wherein the second diameter is less than the first diameter.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Artificial nanopore development is lagging behind protein pore development. One reason is because artificial nanopores with biological nanopore dimensions are challenging to produce. Also, the control over precise structure and chemical functionalities involved in single molecule recognition and interaction are difficult in artificial nanopores. Further, while biological nanopores are genetically designed to position a key chemical feature in a precise location, artificial pores are drilled through a material. Thus, artificial nanopores may result in varying shapes and surface chemistries inside the nanopores, with little or no control over such parameters.

Accordingly, the present disclosure solves the above problems by creating a chemical interface inside an artificial nanopore. The artificial nanopore surface interior includes self-assembled three-dimensional (3D) structures. The surface structures create a scaffold within the nanopore with specific binding sites for chemical functionalities in specific positions within the artificial pore. The disclosed artificial nanopores restore control over the chemical structure of the nanopore inner surface.

As stated above, the present disclosure relates to nanopores, and particularly to artificial nanopores, which are now described in detail with accompanying figures. It is noted that like reference numerals refer to like elements across different embodiments.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant of the invention employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

Figure 1A:
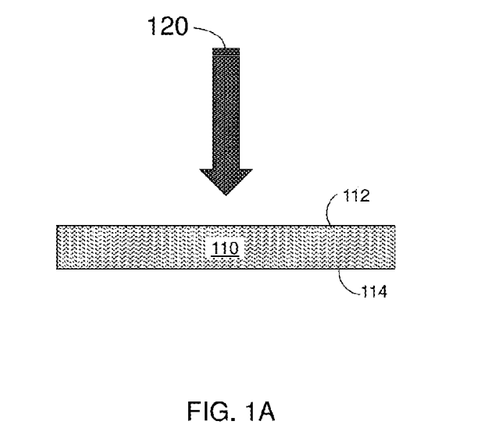
FIG. 1A illustrates a cross-sectional side view of a substrate before gold ion beam drilling.

Referring now to the figures, FIG. 1A illustrates a cross-sectional side view of a nanopore structure's substrate 110 before drilling with a gold ion beam 120. The substrate has a first surface 112 and a second surface 114 opposite the first surface 112.

Non-limiting examples of suitable substrate materials include silicon, silicon oxide, silicon nitride, or any combination thereof. The substrate 110 can include a single layer or multiple layers of any of the aforementioned materials or layers or any additional materials and layers.

The substrate 110 may be fabricated using any suitable fabrication process. Non-limiting examples of suitable fabrication processes include, for example, chemical vapor deposition (CVD), plasma enhanced chemical vapor deposition (PECVD), lithographic patterning and etching, epitaxial growth processes, or any combination thereof.

The thickness of the substrate 110 is not intended to be limited. In one embodiment, the substrate 110 has a thickness in a range from about 10 to about 100 nanometers (nm). In another embodiment, the substrate 110 has a thickness in a range from about 20 to about 50 nm. Yet, in other embodiments, the substrate 110 has a thickness about or in any range from about 10, 25, 50, 75, 100, 125, and 150 nm.

The drilling with a gold ion beam 120 may be focused ion beam (FIB) or another suitable method. A FIB setup uses a focused beam of gold ions for deposition or ablation of materials.

Figure 1B:
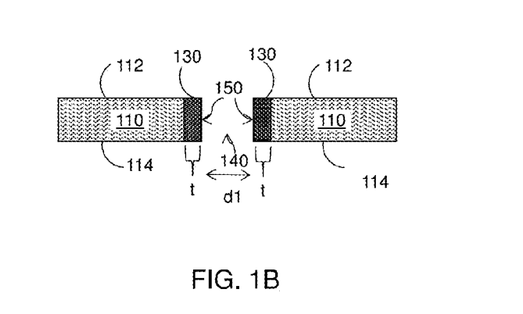
FIG. 1B illustrates a cross-sectional side view of an aperture extending through the substrate of FIG. 1B after gold ion beam drilling.

FIG. 1B illustrates a cross-sectional side view of a nanopore structure having an aperture 140 extending through the substrate 110 of FIG. 1A after drilling with a gold ion beam 120. The aperture 140 extends from the first surface 112 to the second surface 114.

Drilling with a gold ion beam 120 uses a gold ion beam to drill the aperture 140. Gold ions 130 ($Au^{2+}$) heavily contaminate the wall 150 or a portion of the wall 150 of the aperture 140. Gold ions 130 are embedded in the substrate 110 in a region confined to the walls of the aperture 140. The remaining regions of the substrate 110 are substantially free of gold ions. Gold ions are used to create a covalent bound with the thiolated DNA.

The gold ion beam patterning parameters can be adjusted to form an aperture 140 with the desired diameter within the substrate 110. For example, the acceleration voltage, beam current, dwell time per point can be varied. Increasing the dwell time and beam current can increase the diameter of the apertures 140.

The thickness, t, of the embedded gold ions 130 within the substrate 110 can generally vary. In some embodiments, the thickness t of the embedded gold ions 130 is in a range from about 2 to about 40 nm. In one embodiment, the thickness t of the embedded gold ions 130 is in a range from about 5 to about 10 nm. In other embodiments, the thickness t of the embedded gold ions 130 is in a range about or in any range from about 2, 5, 10, 15, 20, 25, 30, 35, and 40 nm.

The wall 150 of the aperture 140 has a diameter d1 (a first diameter) that can generally vary and is not intended to be limited. In one embodiment, the diameter d1 is in a range from about 10 to about 100. In one embodiment, the diameter d1 is in a range from about 20 to about 40. In other embodiments, the diameter d1 is in a range about or in any range from about 10, 20, 30, 40, 50, 60, 70, 80, 90, and 100 nm.

Figure 2A:
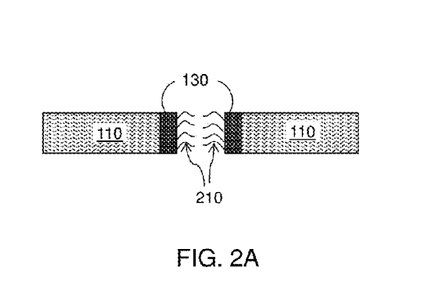
FIG. 2A illustrates a cross-sectional side view of thiolated DNA bound to gold ions within the aperture of FIG. 1A.
Figure 2B:
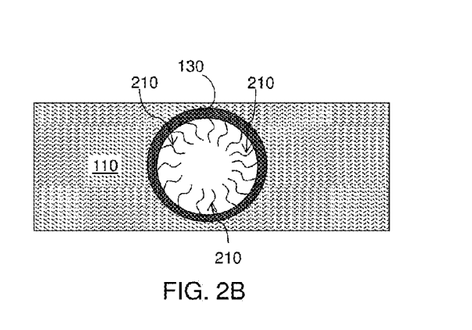
FIG. 2B illustrates a top view of FIG. 2A.

FIG. 2A illustrates a cross-sectional side view of a first DNA layer bound to gold ions 130 within the wall 150 of the aperture 140 of FIG. 1A. FIG. 2B illustrates a top view of FIG. 2A. The first DNA layer includes a thiolated DNA strand 210 chemically bonded to gold ions 130 within the wall 150 of the aperture 140. The thiolated DNA strand 210 includes a thiolate group that covalently bonds to the gold ions 130. The thiolated DNA 210 is a single-stranded DNA strand. One or more thiolated DNA strands 210 binds to the gold ions 130 within the aperture 140. The thiolated DNA strand 210 dangles within the wall 150 aperture 140 and forms an anchor within the aperture 140.

Each thiolated DNA strand 210 has a length that can generally vary. In one embodiment, each thiolated DNA strand 210 has a length in a range from about 30 to about 200 bases. In another embodiment, each thiolated DNA strand 210 has a length in a range from about 60 to about 110 bases.

Figure 3A:
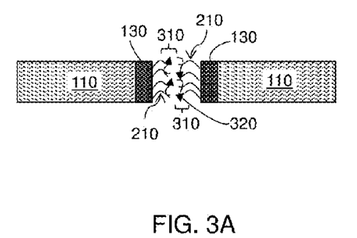
FIG. 3A illustrates a cross-sectional side view of single-stranded DNA hybridized to the thiolated DNA of FIG. 2A.
Figure 3B:
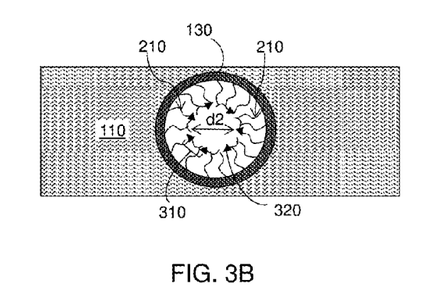
FIG. 3B illustrates a top view of FIG. 3A.

FIG. 3A illustrates a cross-sectional side view of a second DNA layer chemically bonded to the first DNA layer of FIG. 2A via hydrogen bonds. The second DNA layer includes a single-stranded DNA strand 310 that is hydrogen bonded to the thiolated DNA strand 210. FIG. 3B illustrates a top view of FIG. 3A. The single-stranded DNA strand 310 is hybridized (bonded via hydrogen bonds) to the thiolated DNA 210 such that the single-stranded DNA strand 310 defines a substantially cylindrical nanopore within the aperture 140. The single-stranded DNA strand 310 includes biofunctional group binding sites 320 to biofunctionalize the substantially cylindrical nanopore.

The binding sites 320 can be any functional group, chemical functionality, or specific DNA sequence within the single-stranded DNA 310 where biomolecules 410 can be attached. Non-limiting examples of suitable chemical functional groups include alcohols, amines, carboxylates, esters, ethers, amides, thiols, aldehydes, ketones, acyl halides, nitriles, imines, isocyanates, azo compounds, arenes, acid anhydrides, alkanes, alkenes, alkynes, or any combination thereof. The functional groups may be substituted or non-substituted. The functional groups may be charged or uncharged.

The single-stranded DNA strand 310 forms a 3D DNA origami frame inside the aperture 140. As described herein, a 3D DNA origami is the nanoscale folding of DNA to create arbitrary two and three-dimensional shapes at the nanoscale. The DNA origami frame can remain inside the aperture 140 even if the thiolated DNA strand 210 anchor molecules detach from the gold ions 130 embedded in the wall 150 of the aperture 140. The resulting DNA origami frame provides a structure with sequence specific anchor points where specific functionalities can be precisely positioned.

The substantially cylindrical nanopore has a diameter d2 (a second diameter) (see FIG. 3B) that can generally vary and is not intended to be limited. The diameter d2 is less than the diameter d1 of the aperture (the first diameter). In one embodiment, the diameter d2 is in a range from about 5 to about 30 nm. In another embodiment, the diameter d2 is in a range from about 5 to about 15 nm. In other embodiments, the diameter d2 is in a range about or in any range from about 5, 10, 15, 20, 25, and 30 nm.

Figure 4A:
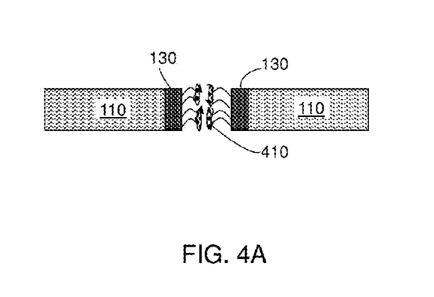
FIG. 4A illustrates a cross-sectional side view of biomolecules bound to the single-stranded DNA of FIG. 3A.
Figure 4B:
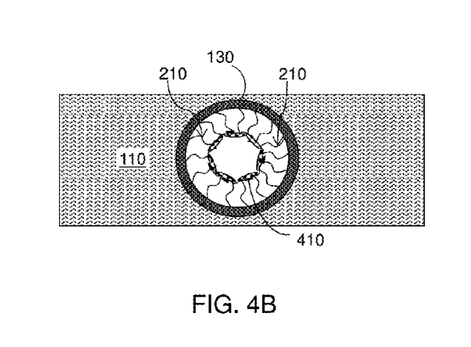
FIG. 4B illustrates a top view of FIG. 4A.

FIG. 4A illustrates a cross-sectional side view of biomolecules 410 bound to the single-stranded DNA strands 310 of FIG. 3A. FIG. 4B illustrates a top view of FIG. 4A. Biomolecules 410 will bind to the biofunctional group binding sites 320. The biomolecules 410 attach to the DNA origami scaffold formed by the single-stranded DNA stand 310 to form a protein-like inner nanopore. The biomolecules 410 provide for wetting and affinity with target analytes. The biomolecules 410 can be chemically bonded to the binding sites 320.

The biomolecules 410 can be any molecule present in living organisms. Non-limiting examples of suitable biomolecules 410 macromolecules, for example, proteins, polysaccharides, lipids, and nucleic acids, and small molecules, for example, primary metabolites, secondary metabolites, and natural products. Other small molecules include, but are not limited to, lipids, fatty acids, glycolipids, sterols, glycerolipids, vitamins, hormones, neurotransmitters, metabolites, monomers, oligomers, polymers, or any combination thereof. The biomolecules 410 can be biomonomers, for example, amino acids, monosaccharides, or nucleotides. The biomolecules 410 can be bio-oligomers, for example, oligopeptides, oligosaccharides, or oligonucleotides. Other non-limiting examples of suitable biomolecules include DNA, ribonucleic acid (RNA), glycolipids, phospholipids, and enzymes.

Figure 5A:
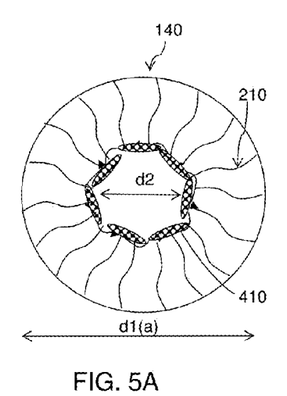
FIGS. 5A, 5B, and 5C respectively illustrate top views of substantially cylindrical nanopores having substantially the same inner diameters within apertures of different diameters.
Figure 5B:
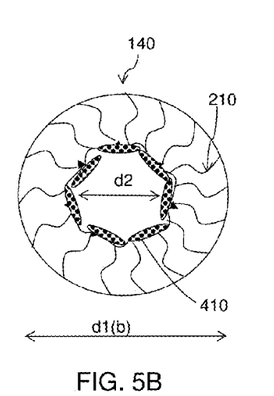
Figure 5C:
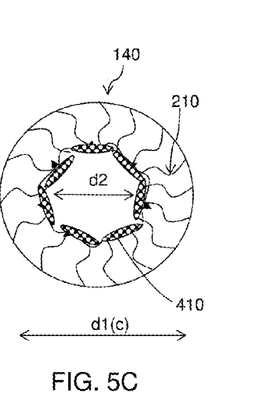

FIGS. 5A, 5B, and 5C illustrate top views of substantially cylindrical nanopores within apertures 140 having different diameters. Each aperture 140 has a first diameter d1(a), d1(b), and d1(c) that generally varies, while the substantially cylindrical nanopore within the aperture 140 has a substantially fixed second diameter d2.

In the exemplary embodiments of FIGS. 5A-5C, the first diameters decrease in size as follows: d1(a)>d1(b)>d1(c). Simultaneously, the second diameters d2 are substantially the same. The thiolated DNA 210 changes length by extending or curling to accommodate for variations in the gold ion drilled aperture diameter d1(a), d1(b), and d1(c). The thiolated DNA 210 has a variable length that depends on the aperture's 140 first diameter d1 and such that the substantially cylindrical nanopore's second diameter d2 is substantially fixed.

Thus substantially cylindrical nanopores, which mirror protein nanopores, can be fitted within an existing artificial nanopore. The approach leaves gaps between the DNA outer structure formed by the thiolated DNA strands 210 and the artificial nanopore structure within, formed by the single-stranded DNA 410.

The disclosed nanopore structures solve the problem caused by variable artificial nanopore structure dimensions, as shown in FIGS. 5A-5C, that result in non-reproducible results. Small variations in artificial nanopore dimensions caused by manufacturing variability and artifacts become more problematic as nanopores become smaller. By forming the DNA nanopore out of the inner structure of the artificial 3D DNA nanopore, specific nanopores with consistent dimensions provide reliable and reproducible results.

Example

To demonstrate the capability of gold ion beam lithography for milling of nanopores in thin membranes, membrane chips were processed using the Raith ionLiNE system (Raith Nano fabrication, Dortmund, Germany). About 100 membranes were ion beam drilled using the Raith multi species development tool.

The patterning parameters were as follows: acceleration voltage 40 kV; beam current 1.4-3.3 pÅ; and dwell time per point 2.5-60 ms.

Figure 6:
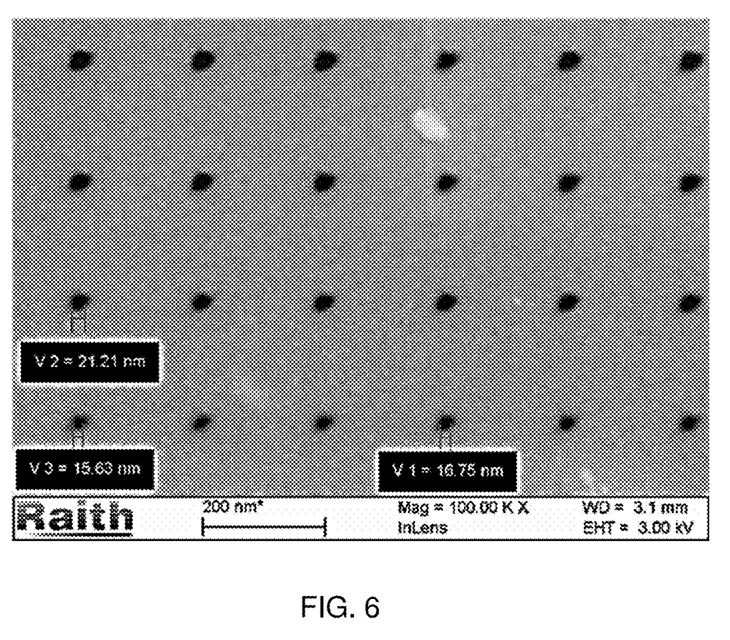
FIG. 6 shows a dose test array membrane milled with $Au^{2+}$ ions at 2.3 picoÅmperes (pÅ) with varying dwell times.

FIG. 6 shows a dose test array membrane milled with $Au^{2+}$ ions at 2.3 picoÅmperes (pÅ). Various dwell times were tested, including 3.5 ms, 3.65 ms, and 4 ms. The resulting apertures had exemplary diameters of 12.21 nm, 15.63 nm, and 16.75 nm.

Figure 7:
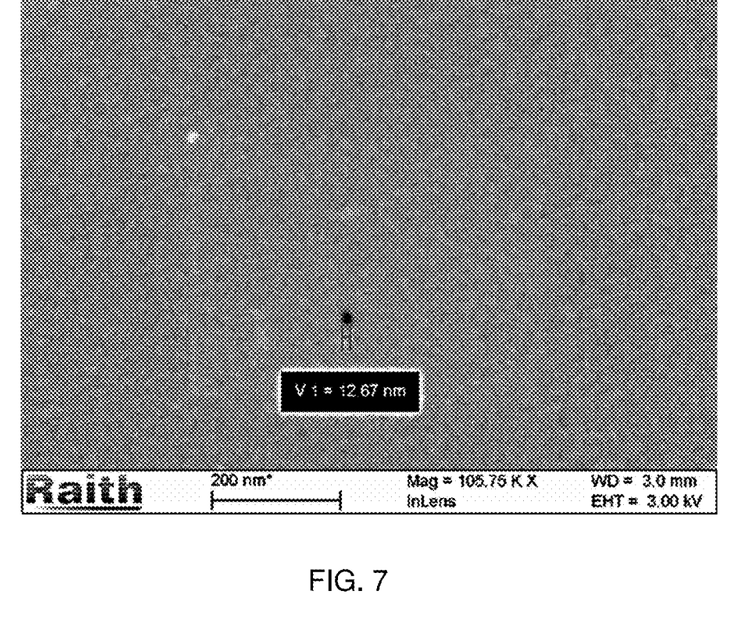
FIG. 7 shows a single pore fabricated by a $Au^{2+}$ beam with a 4.5 ms dwell time at a 2.3 pÅ beam current.

FIG. 7 shows a single pore fabricated by a $Au^{2+}$ beam with a 4.5 ms dwell time at a 2.3 pÅ beam current. The resulting aperture diameter was 12.67 nm.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for making a nanopore structure, the method comprising:
    drilling with a gold ion beam to define an aperture through a substrate and to introduce and embed gold ions within a wall of the aperture, the wall defining a first diameter;
    embedding the gold ions in a region confined to the wall of the aperture to a thickness of about 2 to about 40 nm;
    bonding a thiolated DNA strand to the embedded gold ions with covalent bond; and
    bonding a single-stranded DNA strand to the thiolated DNA strand with a hydrogen bond to define a substantially cylindrical nanopore, the substantially cylindrical nanopore defining a second diameter within the aperture;
    wherein the second diameter is less than the first diameter.

2. The method of claim 1, wherein the single-stranded DNA strand further comprises a biofunctional group binding site.

3. The method of claim 2, wherein the biofunctional group binding site is a DNA sequence within the single-stranded DNA strand.

4. The method of claim 2, wherein the biofunctional group binding site is a chemical functional group is chemically bonded to the single-stranded DNA strand.

5. The method of claim 1, wherein the drilling with a gold ion beam is focused ion beam (FIB) drilling.

6. The method of claim 1, wherein the thiolated DNA strand is a single-stranded DNA strand.

7. The method of claim 1, wherein the substrate is silicon, silicon oxide, silicon nitride, or any combination thereof.

8. The method of claim 1, wherein the first diameter is in a range from about 10 to about 100 nm.

9. The method of claim 1, wherein the second diameter is in a range from about 5 to about 30 nm.

10. A method for making a nanopore structure, the method comprising:
    drilling with a gold ion beam to define an aperture through a substrate and to introduce and embed gold ions within a wall of the aperture, the wall defining a first diameter;
    embedding the gold ions in a region confined to the wall of the aperture to a thickness of about 2 to about 40 nm;
    bonding a first DNA layer to the embedded gold ions within the wall of the aperture via a covalent bond, the first DNA layer comprising a plurality of single-stranded thiolated DNA strands, the plurality of single-stranded thiolated DNA strands of the first DNA layer covalently bonded to the embedded gold ions through a thiolate group, and each single-stranded thiolated DNA strand extending and dangling within the wall of the aperture to form an anchor within the aperture; and
    bonding a second DNA layer to the first DNA layer, the second DNA layer comprising a plurality of single-stranded DNA strands, the plurality of single-stranded DNA strands of the second DNA layer hybridized to the first DNA layer through hydrogen bonds, the second DNA layer defines a substantially cylindrical nanopore that defines a second diameter within the wall of the aperture;
    wherein the second diameter is less than the first diameter, and each single-stranded thiolated DNA strand of the first DNA layer has a variable length that depends on the first diameter of the wall of the aperture such that the second diameter of the substantially cylindrical nanopore is substantially fixed.

* * * * *